United States Patent [19]

Laties et al.

[11] Patent Number: 5,360,801
[45] Date of Patent: Nov. 1, 1994

[54] PHARMACOLOGICAL STIMULATION OF EYE GROWTH

[75] Inventors: Alan M. Laties, Philadelphia; Richard A. Stone, Havertown, both of Pa.

[73] Assignee: The Trustees of The University of Pennsylvania, Philadelphia, Pa.

[21] Appl. No.: 4,685

[22] Filed: Jan. 14, 1993

Related U.S. Application Data

[60] Continuation-in-part of Ser. No. 856,626, Mar. 24, 1992, which is a division of Ser. No. 522,241, May 11, 1990, Pat. No. 5,122,522, which is a continuation of Ser. No. 369,293, Jun. 21, 1989, abandoned.

[51] Int. Cl.$^5$ .................. A61K 31/55; A61K 31/445; A61K 31/415
[52] U.S. Cl. .................. 514/215; 514/323; 514/397; 514/538; 514/642; 514/912
[58] Field of Search ............... 514/215, 323, 397, 642, 514/538, 912

[56] References Cited

U.S. PATENT DOCUMENTS 5,122,522  6/1992  Laties et al. .................. 514/220

OTHER PUBLICATIONS

BioSis Abstract of Annals of ophthamology 20(4) 1988. 133–135.
Weisel & Raviola, "Myopia and Eye Enlargement After Neonatal Lid Fusion in Monkeys", *Nature* 266:66–68.
Schaeffel, F., et al., "Mathematical model of emmetropization in the chicken," *J. Optical Soc. of America*, 5:2080–2086 (1988).
Taylor, Palmer, "Cholinergic Agonists." *Pharmaceutical Basis of Therapeutics*, Ed. Goodman and Gilman. New York: 7th Ed. Macmillan Publ., 1985.
Buckley et al., "Antagonist Binding Properties of Five Cloned Muscarinic Receptors Expressed in CHO-K1 Cells," *Molecular Pharmacology*, 35:469–476 (1989).
Eltze, M., "Muscarinic $M_1$— and $M_2$—receptors mediating opposite effects on neuromuscular transmission in rabbit vas deferens," *European J. of Pharm.*, 151:205–211 (1988).
Micheletti, R, and Schiavone, A., "Functional Determination of McN-A-343 Affinity for $M_1$ Muscarinic Receptors," *Journal of Pharmacology and Experimental Therapeutics*, 253:310–314 (1990).
McBrien, Neville A., et al., "Atropine Reduces Experimental Myopia and Eye Enlargement Via a Nonaccommodative Mechanism," *Investigative Ophthalmology & Visual Science*, 34:205–215 (1993).

*Primary Examiner*—Zohreh Fay
*Attorney, Agent, or Firm*—Woodcock Washburn Kurtz Mackiewicz & Norris

[57] ABSTRACT

A method of inducing axial elongation of an eye of an animal comprising contacting a first open animal eye with a cholinergic agonist, detecting the change in axial growth of the first eye, applying a known control agent in a second open animal eye, observing the results of the control agent on the second eye, and comparing the change in axial growth of the first eye with the change in axial growth of the second eye.

25 Claims, No Drawings

PHARMACOLOGICAL STIMULATION OF EYE GROWTH

REFERENCE TO GOVERNMENT GRANTS

This work was supported in part by research grants from the National Institutes of Health, grant number EY05454. The United States Government may have certain rights in this invention.

This application is a continuation-in-part of application Ser. No. 856,626, filed Mar. 24, 1992 now pending, which is a divisional of application Ser. No. 522,241, filed May 11, 1990, now U.S. Pat. No. 5,122,522, which is a continuation of application Ser. No. 369,293, filed Jun. 21, 1989, now abandoned.

BACKGROUND OF THE INVENTION

This invention relates to modulation of ocular development and, more particularly, to induction of axial elongation of the eye.

At age 6 months, the human eye is about two-thirds adult size and is even at that size relatively short in the axial direction. As a consequence, young children tend to be farsighted. During childhood, as the eye grows, there is a compensatory fine tuning of the optical properties of the cornea and lens to an increasing ocular length. Often the entire process is virtually perfect: no accommodation is needed for sharp vision at distance; the eye is emmetropic. Regulatory failure in this finely tuned process can go in either direction. If it goes toward a lengthened eye, then distant images focus in front of the plane of the retina and axial myopia results. If, on the other hand, the regulatory failure leads to an eye whose ocular length is too short, distant images would focus behind the plane of the retina and the result is hyperopia or farsightedness.

An eye that is axially shorter than average by a small amount and as a consequence hyperopic by a small amount, up to about 2.0 Diopters, is usually of little clinical consequence, except for the need for glasses in the adult. However, hyperopia of more than 2.0 Diopters often requires optical correction even in childhood. In addition, it can lead to problems. For instance it can be accompanied by squint (as it presents in children) due to a well described synergism between the internal focusing and external converging systems of the eye. In effect, the constant demand for focussing power stimulates excess convergence and one eye turns in. This form of hyperopia often requires correction by eyeglasses in early life. The small eye of hyperopia can bring problems in early or later life as well. After age 40 it can be subject to an acute form of glaucoma as a steady increase in lens size (the lens normally grows in anterior-posterior diameter steadily through life) crowds the iris too far forward toward the cornea and thus blocks the outflow pathway for aqueous humor.

Prior work leading to the present invention is scant and only indirectly related, as it concerns:

1) the discovery of an experimental model of myopia induced by deprivation of form vision, usually to one eye. Prior work on visual form deprivation includes:

The discovery by Weisel & Raviola, "*Myopia and Eye Enlargement After Neonatal Lid Fusion in Monkeys*", Nature 266:66 (1977), that the form deprived monkey eye enlarges in the axial dimension and becomes myopic;

U.S. Pat. No. 5,055,302, to Laties and Stone, discloses a method of inhibiting the abnormal postnatal growth of the eye of a maturing animal using vasoactive intestinal peptide (VIP), PH1 or analogues of these peptides. These peptides were found to inhibit axial elongation of a visually deprived myopic eye;

U.S. Pat. No. 5,122,522, to Laties and Stone, discloses a method of inhibiting the abnormal postnatal growth of the eye of a maturing animal using pirenzepine. Axial elongation of a myopic eye was inhibited upon application of pirenzepine; and 2) the discovery that axial eye growth is responsive to the imposition of plus or minus power lenses for a developing eye. A lens that brings the image plane forward retards axial elongation and one that moves the image back enhances axial eye elongation. One example is supplied by the work of Schaeffel, F., et al., *J. Optical Soc. of America*, 5: 2080, (1988).

In a clear departure from the vision form deprivation work, the present invention derives from experiments in chicks that are not visually manipulated in any way; that instead have both eyes open from birth and are permitted unimpaired vision. The present invention discloses a method to enhance the growth of a developing eye in the axial dimension. Also, axial elongation by cholinergic agonists is found to be inhibited by cholinergic antagonists and dopamine agonists.

SUMMARY OF THE INVENTION

In accordance with this invention, a method of enhancing axial elongation of an eye of an animal comprising contacting a first open animal eye with a cholinergic agonist, detecting the change in axial growth of a first eye, applying a known control agent in a second open animal eye, observing the results of a control agent on a second eye, and comparing a change in axial growth of a first eye with a change in axial growth of a second eye is provided. This invention is more particularly pointed out in the appended claims and is described in its preferred embodiments in the following description.

DETAILED DESCRIPTION OF THE INVENTION

In the ordinary visual function of the eye of an animal, light forming an image passes through the lens and is received by the retina, a neural tissue embryologically related to the brain. The retina transmits this information to the optic nerve which sends it on to the brain.

Retinal neurochemicals (i.e., neuro-active chemical compounds) are key ingredients in the vision process. Specifically, light forming the image is sensed by the light receptors, the rods and cones, of the retina. These photoreceptors act as transducers changing light energy into electrical and/or chemical signals.

In the regular process of transmitting the image information to the brain, the photoreceptors, in association with retinal nerve cells, release neurochemicals and pass electrical signals transmitting information to adjacent retinal cells as parts of a network in the retina leading to the formulation and qualities of the signals that later go to the brain via optic nerve.

The present invention is directed to a method of enhancing axial growth of the developing eye or eyes of a juvenile animal comprising contacting an open animal eye with a cholinergic agonist, detecting the elongation in axial growth of the eye, contacting a second open animal eye with a known control agent, observing the results of the second eye, and comparing the elongation in axial growth of said first eye with the change in axial growth of said second eye. The enhancement of axial growth by cholinergic agonists may be detected by the method of the present invention. The second eye may be the contralateral eye of the animal.

Alternatively, the axial growth of both eyes of one animal may be enhanced. In this case to demonstrate the effect, both eyes of a treated animal are matched with the untreated eyes of another animal. Thus, the matched pairs of open eyes of the two animals are arranged thereby having the first eye and the second eye of the first animal compared with the first eye and the second eye of the second animal, the axial lengths of the eyes of the first and second animals are measured, the first and second eyes of the first animal are contacted with a cholinergic agonist, the change in axial growth of the eyes of the first animal is detected, a known control agent is applied to the first and second eyes of the second animal, the change in axial growth of the eyes of the second animal is observed, and said change in axial growth of said first eyes of said first animal and said second animal and said change in axial growth of said second eyes of said first animal and said second animal are compared.

A method of detecting the inhibition of response of an animal eye to a pharmacological agent is also an embodiment of the present invention. Cholinergic antagonists and dopamine agonists inhibit the ability of cholinergic agonists to enhance elongation of animal eyes when one of the former are co-administered with a cholinergic agonist.

In accordance with the present invention, enhance refers to an increase and/or induction in axial growth. More specifically, enhance refers to the ability of a cholinergic agonist to elongate growth of the eye or eyes of an animal in the axial direction. Enhancement of axial elongation by diverse cholinergic agonists, including and not limited to carbamyl choline chloride, pilocarpine and McNeil-A-343, has been detected with the chick open eye model. The cholinergic agonist axial elongation inhibition by cholinergic antagonists, such as and not limited to atropine and pirenzepine, and dopamine agonists, such as and not limited to apomorphine, has been detected through the use of the chick open eye model.

It has been found that the invention provides a rapid and effective drug screening method for agents of two kinds, those which enhance axial growth and those that inhibit axial growth. In accordance with the present invention, the open eye model provides an inexpensive, easy method of obtaining results from a large sample population. While one animal for use in the model is birds, such as and not limited to chicks, other animals including primates and mammals such as and not limited to juvenile monkeys and humans, are included within the scope of the invention. Chicks mature rapidly and a drug assay may be accomplished in a matter of weeks. Chicks are permitted normal full vision in each eye from birth. The model is ultimately for use and benefit of humans. The method of the present invention, as used for humans, provide the cholinergic agonists, cholinergic antagonists and dopamine agonists at therapeutically effective and therapeutically determined concentrations or dosages. The concentrations for humans or other animals may be determined by extrapolation from the in vivo chick data disclosed herein. Particularly for humans, the concentrations of cholinergic agonists, antagonists and dopamine agonists for use in the present invention are in the range of from about 0.01% to about 5%, more commonly from about 0.25% to about 1.0%. The inhibition by cholinergic antagonists and dopamine agonists of axial growth, which is induced by cholinergic agonists, may also be detected by the method of the present invention. The agonists and antagonists for use in the present invention may be administered in a pharmaceutically acceptable ophthalmic carrier, including and not limited to those known ophthalmic buffered solutions having no medically unacceptable side effects, such as a water-based eye drop solution, having a pH of about 6.5 and practical in terms of known solubility and stability.

In the chick open eye model, a cholinergic agonist is delivered to one eye of the animal. Another eye, which may be the contralateral eye or an eye of another animal serves as the control. A vehicle such as saline is added to this second eye. It has been found that under certain circumstances, local administration of a cholinergic agonist to one eye of an animal with both eyes open and vision unimpeded, leads to a selective axial elongation of the treated eye. A description of cholinergic agonists is contained in Chapter 5 "Cholinergic Agonists" by Palmer Taylor in *Pharmaceutical Basis of Therapeutics*, 7th Ed. Macmillan Publ. (1985) edited by Goodman and Gilman. Specifically, cholinergic agonists carbachol (carbamyl choline chloride, i.e., 2-[(aminocarbonyl)]-N,N,N,- trimethylethanammonium chloride), pilocarpine (3-ethyldihydro-4-(1-methyl-1H-imidazol-5-yl) [methyl]-2(3H)-furanone), and the $m_1$ muscarinic agonist McNeil-A-343 (the compound (4-hydroxy-2-butynyl)-1-trimethylammonium m-chlorocarbanilate chloride), were administered on a once a day regimen. At the conclusion of the experiment, the drug-treated eyes were longer than vehicle-treated (control) fellow eyes.

In chicks as well as in humans, axial elongation in both eyes can be documented by comparing matched pairs of eyes of one animal with the eyes of another animal. Particularly, detecting the ability of a cholinergic agonist to induce axial growth of both eyes of an animal comprises contacting the open animal eyes with said cholinergic agonist, detecting the change in axial growth of the eyes, contacting the eyes of the other animal with a control agent and measuring the change in axial growth of the eyes, and comparing said change in axial growth of the eyes of the animal treated with the cholinergic agonist with the change in axial growth of the eyes of the animal treated with the control.

In accordance with the present invention, the enhancement of axial growth by cholinergic agonists may be inhibited by certain pharmacological agents. Any agent which may safely be co-administered to an animal eye along with a cholinergic agonist, and which inhibits or reverses axial elongation by cholinergic agonists is herein referred to as a pharmaceutical agent. Such pharmacological agents include, and are not limited to cholinergic antagonists and dopamine agonists. Cholinergic agonists include the non-limiting group carbamyl choline chloride (carbachol), pilocarpine and (4-hydroxy-2-butynyl)-1-trimethylammonium-m-chlorocarbanilate chloride (McNeil-A-343).

It should also be noted that there are two grounds to support the claim that the muscarinic system is responsible for axial elongation and that inhibition of expected axial elongation is of the type commonly designated $M_1$. Evidence for an $M_1$ designation derives from the demonstration in open eye chicks that: 1) the $M_1$ selective agonist McNeil A-343 induces axial elongation and 2) that the $M_1$ selective antagonist pirenzepine blocks expected axial elongation after agonist stimulation thereof.

It is common to administer these pharmaceutical agents in the form of their salts, e.g., hydrochlorides or nitrates, or less commonly, their esters or as pro-drugs.

In accordance with the present invention, the chick open eye model is also useful in screening for the ability of anticholinergic muscarinic antagonists and dopamine agonists to block axial elongation by cholinergic agonists. Cholinergic antagonists of the present invention include, and are not limited to, pirenzepine and atropine. Dopamine agonists include, and are not limited to, apomorphine. These selected cholinergic antagonists and dopamine agonists inhibit axial elongation which may be induced by cholinergic agonists carbachol, pilocarpine and McNeil-A-343.

As stated herein, some of the cholinergic agonists for use in this invention are non-selective, that is agonists, in the case of pilocarpine and carbachol, that are known to stimulate all subtypes of muscarinic receptors with moderate differences in effectivity toward any one. The cholinergic agonist McNeil A-343, however, is considered selective for $M_1$ receptors. The relative affinity of cholinergic agonists and antagonists for $m_1$–$m_5$ receptors can be determined by means known in the art. See Buckley et al., *Molecular Pharmacology*, 35: 469–476 (1989) for a description of antagonist binding properties of five cloned muscarinic receptors and Eltze, M., *European J. of Pharm.*, 151: 205–211 (1988) for a description of agonist binding properties. Similarly there are many ways in which to accomplish functional studies to measure $m_1$ sensitivity. For instance, one method at present is to use vas deferens of the guinea pig which has an $M_1$ sensitivity. Micheletti, R, and Schiavone, A., *Journal of Pharmacology and Experimental Therapeutics*, 253: 310–314 (1990).

The case of the present invention lies in the discoveries that topical local application of drug to a normally seeing eye of a young chick can enhance eye growth. Cholinergic agonist drugs, such as carbachol, pilocarpine and McNeil-A-343 stimulate axial elongation in the open eye model. The degree of eye growth enhancement in turn is susceptible to modulation by co-administration of yet other pharmacological agents. The growth effect of these cholinergic agonists can be inhibited by co-administration of cholinergic antagonists and dopamine agonists as witnessed in the open eye model of the present invention.

This invention is now described by the following examples. The examples are not to be construed as limiting the scope of the appended claims.

EXAMPLE 1

Open eye axial elongation was induced in day-old White Leghorn chicks under aseptic conditions. All injections are performed under ether anesthesia. The cholinergic agonist carbachol was added to one eye of a chick by subconjunctival injection (0.15 µg). Nine chicks in the sample population were given carbachol. Saline solution was delivered by subconjunctival injection to the non-drug treated eye of the same chick which received carbachol. The experiment was repeated for pilocarpine (2.0 µg-7 chicks, 0.2 µg-10 chicks and 0.02 µg-9 chicks) and McNeil-A-343 (0.3 µg-10 chicks), see TABLE I. Atropine (0.5 µg-7 chicks) and pirenzepine (0.3 µg-8 chicks) were given to other open chick eyes in the same method of administration, see TABLE II.

The chicks were maintained on a 12 hour light:dark cycle with both eyes open. Drugs were delivered daily during the light cycle. At two weeks of age the animals were sacrificed and axial and equatorial dimensions of unfixed eyes were measured with vernier calipers independently by two observers. Chick open eyes treated with carbachol, pilocarpine and McNeil-A-343 developed significant axial elongation (0.09 mm±0.04 to 0.20 mm±0.032, see TABLE I) while those treated with pirenzepine or atropine exhibited no significant growth difference (−0.04 mm±0.06 to 0.04 mm±0.02, see TABLE II). The average increase in axial length is the difference between deprived eye minus contralateral eye, for the number (n) of animals tested.

TABLE 1

Cholinergic Agonists Enhance Axial Growth of Open Eyes

Ocular Dimensions (mean ± S.E.M.) drug-treated minus vehicle-treated eye

| Drug | Daily Dose (µg) | Axial Length Difference (mm) | Equatorial Diameter Difference (mm) | n |
|---|---|---|---|---|
| carbachol | 0.15 | 0.20 ± 0.032* | 0.07 ± 0.04 | 9 |
| pilocarpine | 2.0 | 0.09 ± 0.04* | −0.004 ± 0.03 | 7 |
|  | 0.2 | 0.11 ± 0.03* | −0.02 ± 0.03 | 10 |
|  | 0.02 | 0.18 ± 0.08* | 0.05 ± 0.04 | 9 |
| McN-A-343 | 0.3 | 0.18 ± 0.08* | −0.04 ± 0.02 | 10 |

*By univariate F test, significant treatment effects on axial length are identified for carbachol ($p < 0.001$), pilocarpine in 0.2 µg ($p < 0.05$), 0.2 µg ($p < 0.01$) and in 0.02 µg ($p < 0.05$), and McN-A-343 ($p < 0.05$).

TABLE II

Cholinergic Antagonists Have No Effect on Growth of Open Eyes When Used Alone

| Drug | Daily Dose (µg) | Axial Length Difference (mm) | Equatorial Diameter Difference (mm) | n |
|---|---|---|---|---|
| atropine | 0.5 | −0.04 ± 0.06 | 0.03 ± 0.05 | 7 |
| pirenzepine | 0.3 | 0.04 ± 0.02 | −0.003 ± 0.01 | 8 |

EXAMPLE 2

In order to test the ability of cholinergic antagonists and dopamine agonists to inhibit axial elongation induced by cholinergic agonists, cholinergic agonists and the appropriate drug were co-administered as follows. Carbachol (0.15 µg) and pirenzepine (0.3 µg) were co-administered by subconjunctival injection to one open eye of day old White Leghorn chicks (sample population = 8 chicks). Saline solution was delivered by subconjunctival injection to the non-drug treated eye of the same chick which received carbachol/pirenzepine. The experiment was repeated for coadministration to 8 chicks of carbachol (0.15 µg) and apomorphine (0.25 µg); and co-administration to 9 chicks of McNeil-A-343 (0.3 µg) and atropine (0.5 µg). The chicks were maintained on a 12 hour light:dark cycle with both eyes open. Drugs were delivered daily during the light cycle. At two weeks of age the animals were sacrificed and axial and equatorial dimensions of unfixed eyes were measured with vernier calipers independently by two observers. Chick open eyes treated with co-administered cholinergic agonist and either cholinergic antagonist or dopamine agonist did not increase in axial length, see TABLE III.

TABLE III

Blockade of Cholinergic Agonist Enhancement of Growth of Open Eyes by Co-Administration of Cholinergic Antagonist or Dopamine Agonist

| Drug | Daily Dose (μg) | Ocular Dimensions (mean ± S.E.M.) drug-treated minus vehicle-treated eye | | n |
|---|---|---|---|---|
| | | Axial Length Difference (mm) | Equatorial Diameter Difference (mm) | |
| carbachol + pirenzepine* | 0.15 0.3 | 0.06 ± 0.04 | 0.02 ± 0.03 | 8 |
| carbachol + apomorphine** | 0.15 0.25 | −0.03 ± 0.05 | 0.05 ± 0.04 | 8 |
| McN-A-343 + atropine* | 0.3 0.5 | 0.07 ± 0.06 | −0.06 ± 0.04 | 9 |

** = dopamine agonist
* = cholinergic antagonist

There are no significant treatment effects on the axial and equatorial length by any of these combination regimens of carbachol+pirenzepine, carbachol+apomorphine, McN-A-343+atropine and on all of the equatorial diameter.

The cholinergic agonist induced increase in axial length observed in the open-eye experiments could be important in the treatment of one or both eyes of children with abnormally small eyes, conditions that lead to abnormally small eyes and for individuals with farsightedness (hyperopia) based on inadequate axial length of the eye.

In experiments in animals such as those mentioned hereinabove in which axial myopia has been experimentally induced, it has been noted by others in primates that amblyopia was also experimentally and coincidentally induced. Amblyopia is evidenced by poor visual acuity in the eye resulting in poor visual performance. Normally, visual acuity improves during maturation. It is also known that amblyopia may occur in humans from unknown causes or as part of strabismus, especially in farsighted children with small eyes. As in the case of eye growth and development, it is likely that administration of therapeutically effective amounts and dosages of the muscarinic agonists either relatively selective in stimulating the $M_1$ cholinergic receptors or less selective in stimulating individual types of cholinergic muscarinic receptors such as carbachol or pilocarpine, might prevent or inhibit the development of permanent or persistent amblyopia in maturing humans. It is also possible that humans who have already developed amblyopia from other or even unknown causes might have their amblyopia alleviated by similar therapeutic treatment with the aforementioned agents.

Various modifications of the invention in addition to those shown and described herein will be apparent to those skilled in the art from the foregoing description. Such modifications are also intended to fall within the scope of the appended claims.

What is claimed:

1. A method of enhancing axial elongation of an eye of an animal comprising:
   a. contacting a first open animal eye with a therapeutically effective amount of a cholinergic agonist,
   b. detecting the change in axial growth of said first eye,
   c. applying a known control agent in a second open animal eye,
   d. observing the results of said control agent on said second eye, and
   e. comparing said change in axial growth of said first eye with said change in axial growth of said second eye.

2. The method of claim 1 wherein said cholinergic agonist is selected from the group consisting of carbamyl choline chloride, pilocarpine and McNeil-A-343.

3. The method of claim 1 wherein said second eye is the contralateral open eye of said animal.

4. The method of claim 1 wherein said control agent is a saline.

5. The method of claim 1 wherein said animal is selected from the group consisting of birds, mammals and primates.

6. The method of claim 1 comprising enhancing axial elongation of both eyes of an animal.

7. A method of enhancing axial elongation of the eyes of an animal comprising:
   a. arranging matched pairs of open eyes of two animals thereby having a first animal with a first eye and a second eye and a second animal with a first eye and a second eye,
   b. measuring the axial length of the eyes of said first and said second animals,
   c. contacting said first eye and said second eye of said first animal with a therapeutically effective amount of a cholinergic agonist,
   d. detecting the change in axial growth of said first eye and said second eye of said first animal,
   e. applying a known control agent to said first eye and said second eye of said second animal,
   f. observing the change in axial growth of said first eye and said second eye of said second animal, and
   g. comparing said change in axial growth of said first eyes of said first animal and said second animal and said change in axial growth of said second eyes of said first animal and said second animal.

8. The method of claim 7 wherein said cholinergic agonist is selected from the group consisting of carbamyl choline chloride, pilocarpine and McNeil-A-343.

9. The method of claim 7 wherein said control agent is a saline.

10. The method of claim 7 wherein said animal is selected from the group consisting of birds and primates.

11. A method of detecting the ability of a cholinergic agonist to enhance axial growth of the eye of an animal comprising:
   a. contacting a first open animal eye with a therapeutically effective amount said cholinergic agonist,
   b. detecting the change in axial growth of said first eye,
   c. applying a known control agent in a second open animal eye,
   d. observing the results of said control agent on said second eye, and
   e. comparing said change in axial growth of said first eye with said change in axial growth of said second eye.

12. The method of claim 11 wherein said cholinergic agonist is selected from the group consisting of carbamyl choline chloride, pilocarpine and McNeil-A-343.

13. The method of claim 11 wherein said second eye is the contralateral open eye of said animal.

14. The method of claim 11 wherein said control agent is a saline.

15. The method of claim 11 wherein said animal is selected from the group consisting of birds and primates.

16. The method of claim 11 comprising detecting enhancement of axial growth of both eyes of an animal.

17. A method of detecting the ability of a pharmacological agent to inhibit axial elongation of the eye of an animal otherwise enhanced with a cholinergic agonist comprising:
   a. co-administering to a first open animal eye a therapeutically effective amount of cholinergic agonist and an agent selected from the group consisting of a cholinergic antagonist and a dopamine agonist,
   b. detecting the change in axial growth of said first eye,
   c. applying a known control agent in a second open animal eye,
   d. observing the results of said control agent on said second eye, and
   e. comparing said change in axial growth of said first eye with said change in axial growth of said second eye.

18. The method of claim 17 wherein said cholinergic antagonist is pirenzepine and said cholinergic agonist is carbamyl choline chloride.

19. The method of claim 17 wherein said dopamine agonist is apomorphine and said cholinergic agonist is carbamyl choline chloride.

20. The method of claim 17 wherein said cholinergic antagonist is atropine and said cholinergic agonist is McNeil-A-343.

21. The method of claim 17 wherein said control agent is saline.

22. The method of claim 17 wherein said second eye is the contralateral open eye of said animal.

23. The method of claims 1, 7, or 11, wherein said cholinergic agonist is administered in a pharmaceutically acceptable ophthalmic carrier.

24. The method of claim 17, wherein said pharmacological agent and said cholinergic agonist are independently administered in a pharmaceutically acceptable ophthalmic carrier.

25. A method of using an $M_1$ muscarinic antagonist to lessen an otherwise expected axial elongation of an eye.

* * * * *

UNITED STATES PATENT AND TRADEMARK OFFICE
CERTIFICATE OF CORRECTION

PATENT NO. : 5,360,801
DATED : November 1, 1994
INVENTOR(S) : Laties et al.

It is certified that error appears in the above-indentified patent and that said Letters Patent is hereby corrected as shown below:

Column 8, line 49, insert --of-- after "amount"

Column 8, line 50, delete "be" and insert --b.--

Signed and Sealed this

Twenty-seventh Day of June, 1995

Attest:

BRUCE LEHMAN

Attesting Officer
Commissioner of Patents and Trademarks